(12) United States Patent
Schöb

(10) Patent No.: US 6,220,832 B1
(45) Date of Patent: Apr. 24, 2001

(54) CENTRIFUGAL PUMP AND CENTRIFUGAL PUMP SYSTEM

(75) Inventor: Reto Schöb, Volketswil (CH)

(73) Assignees: Sulzer Electronics AG, Winterthur (CH); Lust Antriebstechnik GmbH, Lahnau (DE)

( * ) Notice: Subject to any disclaimer, the term of this patent is extended or adjusted under 35 U.S.C. 154(b) by 0 days.

(21) Appl. No.: 09/137,266

(22) Filed: Aug. 20, 1998

(30) Foreign Application Priority Data

Sep. 25, 1997 (EP) .................................................. 97810706

(51) Int. Cl.$^7$ .............................. F04B 17/00; A61M 1/00
(52) U.S. Cl. .............................................. 417/423.5; 623/3
(58) Field of Search .............................. 417/423.5, 423.6, 417/423.7, 356, 420; 604/7; 623/4, 3

(56) References Cited

U.S. PATENT DOCUMENTS

| | | |
|---|---|---|
| 2,700,343 | 1/1955 | Pezzillo . |
| 3,272,129 | 9/1966 | Leopold . |
| 4,135,253 * | 1/1979 | Reich et al. ............................. 3/1.7 |
| 4,526,507 | 7/1985 | Bingler . |
| 4,786,240 * | 11/1988 | Koroly et al. ....................... 417/413 |
| 4,984,972 * | 1/1991 | Clausen et al. ..................... 417/420 |
| 5,055,005 | 10/1991 | Kletschka . |
| 5,211,546 * | 5/1993 | Isaacson et al. .................... 417/356 |
| 5,385,581 * | 1/1995 | Bramm et al. .......................... 623/3 |
| 5,399,074 | 3/1995 | Nose . |
| 5,443,503 * | 8/1995 | Yamane .................................... 623/3 |
| 5,470,208 * | 11/1995 | Kletschka ............................. 417/356 |
| 5,685,700 * | 11/1997 | Izraelev ............................... 417/423.7 |
| 5,713,727 * | 2/1998 | Veronesi et al. ..................... 417/356 |
| 5,725,357 * | 3/1998 | Nakazeki et al. ...................... 417/18 |
| 5,797,731 * | 8/1998 | Kobayashi et al. .................. 417/238 |
| 5,924,848 * | 7/1999 | Izraelev ................................ 417/420 |

FOREIGN PATENT DOCUMENTS

| | | |
|---|---|---|
| 924 188 | 2/1955 | (DE) . |
| 0447106A2 | 9/1991 | (EP) . |
| WO 94/13955 | 6/1994 | (WO) . |
| WO 96/31934 | 10/1996 | (WO) . |

OTHER PUBLICATIONS

Gupta, O.R., et al., "Double Inlet Pump" in IBM Technological Disclosure Bulletin, vol. 13, No. 12, May 1971, p. 3710 XP002058163.

* cited by examiner

*Primary Examiner*—Teresa Walberg
*Assistant Examiner*—Daniel Robinson
(74) *Attorney, Agent, or Firm*—Townsend and Townsend and Crew LLP

(57) ABSTRACT

A centrifugal pump for delivering a fluid has a pump housing that comprises a first and a second inlet as well as a first and a second outlet for the fluid, a magnetically mounted impeller located inside pump housing, said impeller being rotatable around a rotation axis, and comprising a magnetically active rotor in the shape of a disk or ring, as well as two sets of vanes, with one set of vanes being provided on each of the two axial boundary surfaces of rotor. The two outlets are offset with respect to one another in the axial direction.

17 Claims, 6 Drawing Sheets

CENTRIFUGAL PUMP AND CENTRIFUGAL PUMP SYSTEM

BACKGROUND OF THE INVENTION

1 Field of the Invention

The invention relates to a centrifugal pump for delivering a fluid as well as to a centrifugal pump system. The invention relates in particular to a centrifugal pump and a centrifugal pump system for delivering blood.

2 Description of the Prior Art

WO-A-96/31934 teaches a rotary pump and especially a centrifugal pump in which the impeller is mounted to float inside the pump housing by magnetic forces, and driven by a rotating field generated by a stator located outside the pump housing. According to the principle of the so-called bearingless motor, the stator is designed as a bearing and drive stator and the rotor is integrated into the impeller and designed as a bearing and drive rotor. Pumps of this kind are especially advantageous for those applications in which the fluid to be delivered must not be contaminated, for example for delivering biological fluids such as blood or highly purified fluids such as super-pure water. Rotary pumps of this kind are also suitable for delivering aggressive fluids, which would destroy mechanical bearings in a short time. Centrifugal pumps of this kind are used, for example, as blood pumps to maintain circulation during open heart surgery. It is also possible to use such pumps as artificial hearts. In this case, it is necessary to use at least two separate pumps. One pump takes over the function of the left ventricle and keeps the systemic circulation functioning while the other pump takes over the function of the right ventricle and maintains the pulmonary circulation. The use of at least two separate pumps to perform the heart function, however, involves a relatively large space requirement that proves to be a limitation especially when it comes to implantation of such pumps as artificial hearts.

SUMMARY OF THE INVENTION

Hence, one goal of the present invention is to provide a centrifugal pump that can deliver the fluid in two different fluid systems. The centrifugal pump must be as compact as possible and permit a high delivery capacity. In particular, it must also be able to be used as a blood pump that can assume the function of the heart. Another goal of the invention is to provide a pump system that offers considerable safety against operating problems.

By the arrangement of the outlets according to the invention, namely offset from one another in the axial direction, the centrifugal pump according to the invention can assume the function of two pumps. By means of the first set of vanes, it delivers the fluid from the first inlet to the first outlet and by means of the second set of vanes delivers the fluid from the second inlet to the second outlet. Thus, the centrifugal pump according to the invention can deliver fluid in two different fluid systems.

The centrifugal pump system with at least two centrifugal pumps allows a considerable degree of safety. Each of the two centrifugal pumps alone can deliver the fluid into the two fluid systems so that even if one of the two centrifugal pumps should fail, the other centrifugal pump ensures the functionality of the centrifugal pump system. This redundancy is especially advantageous for medical applications.

DETAILED DESCRIPTION OF THE PREFERRED EXEMPLARY EMBODIMENTS

Figure 1:
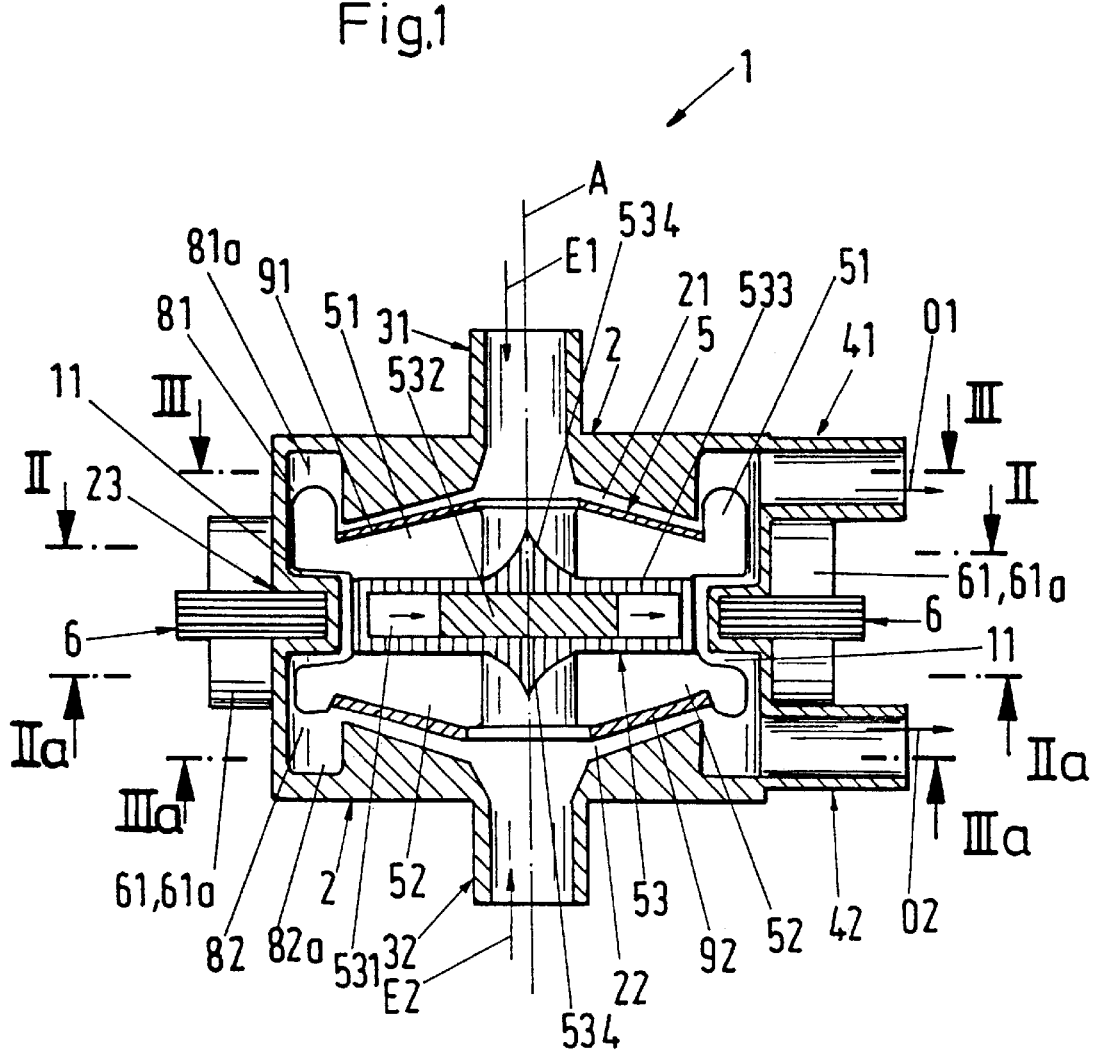
FIG. 1: a lengthwise section through a first embodiment of the centrifugal pump according to the invention.

In the following description, which is of an exemplary nature, reference will be made to the application in which the centrifugal pump or centrifugal pump system according to the invention is used as a blood pump to assume cardiac function. However, it is understood that the centrifugal pump or the system according to the invention is not limited to such applications. It is also suitable, in particular, for delivering other biological fluids, highly pure fluids such as super-pure water, or aggressive fluids.

The centrifugal pump according to the invention for delivering a fluid, especially for delivering blood, has a pump housing 2 (FIG. 1) that has a first and a second inlet 31 and 32 respectively, as well as a first and second outlet 41 and 42, respectively, for the fluid. A magnetically supportable impeller 5 is located inside pump housing 2, said impeller being rotatable around a rotation axis A, and comprising a magnetically effective rotor 53 in the shape of a disk or ring, as well as two sets of vanes 51 and 52, with one set of vanes 51 or 52 being provided on each of the two axial boundary surfaces of rotor 53. The two outlets 41 and 42 are located offset with respect to one another in the axial direction.

The term "centrifugal pumps" refers to those rotary or centrifugal pumps in which the fluid to be delivered flows toward rotation axis A to impeller 5 and leaves the pump housing 2 in the radial or tangential direction.

In an especially preferred embodiment of the centrifugal pump according to the invention, impeller 5 is mounted magnetically and with zero contact in pump housing 2 and driven by an electromagnetic rotating field. For this purpose, the passive magnetically effective rotor 53, which is part of impeller 5, as well as a stator 6 surrounding pump housing 2, and having electrical windings 61 is provided. Stator 6 is preferably designed as a bearing and drive stator so that impeller 5 in the operating state is both drivable by the magnetic interaction between stator 6 and rotor 53 and can also be mounted with zero contact in pump housing 2. Preferably, stator 6 and rotor 53 form a so-called bearingless motor which can be designed in a manner similar to that disclosed in WO-A-96/31934. The function and the design as regards drive and magnetic bearings for rotor 53 are described in detail in this publication, whose content is hereby incorporated into this specification, and will therefore not be described in greater detail here.

In the following, the most important features of the principle of the bearingless motor are summarized briefly. The term "bearingless motor" refers to an electrically controllable bearing and drive device that comprises stator 6 and rotor 53. The term "bearingless motor" is intended to show that stator 6 is simultaneously the drive and bearing stator, in other words, no separate stator (nor any separate rotor) is provided for the magnetic bearing. Stator 6 is so designed and provided with electrical windings 61 that it generates an electromagnetic rotating field which firstly exerts a torque on rotor 53 such that its rotation drives rotation axis A and also exerts an adjustable transverse force on rotor 53 so that its position relative to a plane perpendicular to rotation axis A can be determined or controlled actively. Thus, rotor 53 can be controlled or driven in the operating state by means of electrical windings 61 of stator 6 in three degrees of freedom, namely rotation around rotation axis A and position relative to the plane perpendicular to rotation axis A (two degrees of freedom). For this purpose, electrical windings 61 of stator 6 include, for example, a drive winding with a pole pair number p and a control winding with a pole pair number p+1 or p−1.

With respect to three additional degrees of freedom, namely tilting relative to the plane perpendicular to rotation axis A (two degrees of freedom) and axial position, rotor 53 is preferably mounted magnetically passively by reluctance forces, in other words, in a uncontrollable manner in stator 6. For this purpose, stator 6 has several teeth extending radially inward (not shown). For further details of the design and control of stator 6 or the design of rotor 53, reference is made here to WO-A-96/31934. The explanations to be found therein regarding the drive and mounting can be used in similar fashion for the centrifugal pump according to the invention.

Figure 2:
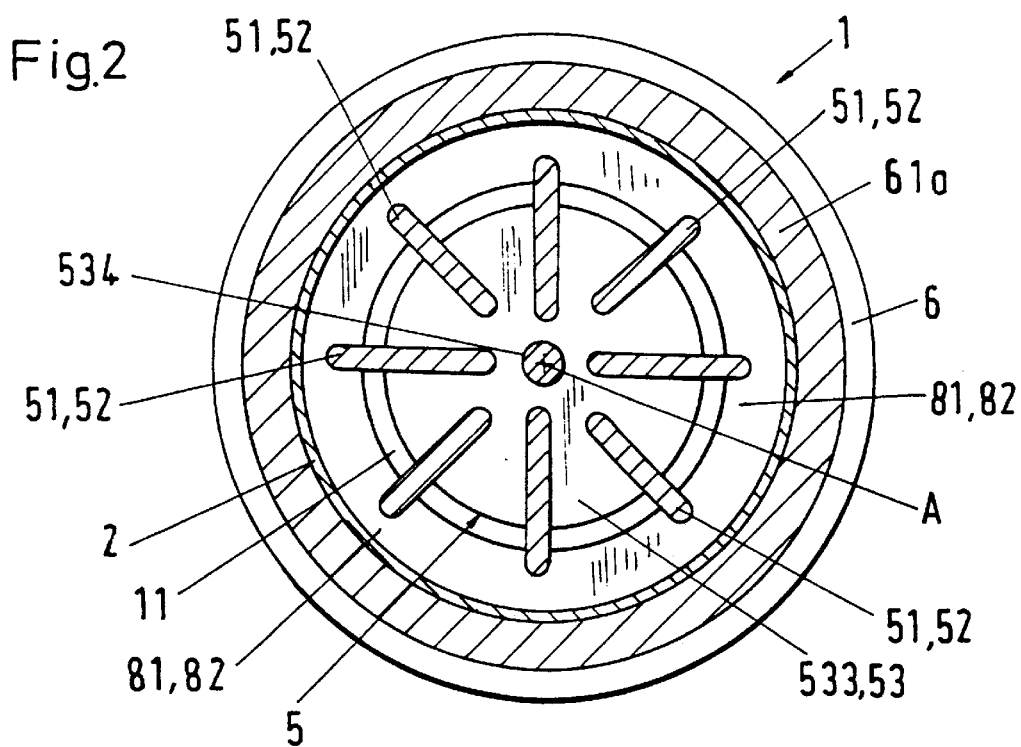
FIG. 2: a cross section through the first embodiment along section lines II—II and IIa—IIa in FIG. 1.
Figure 3:
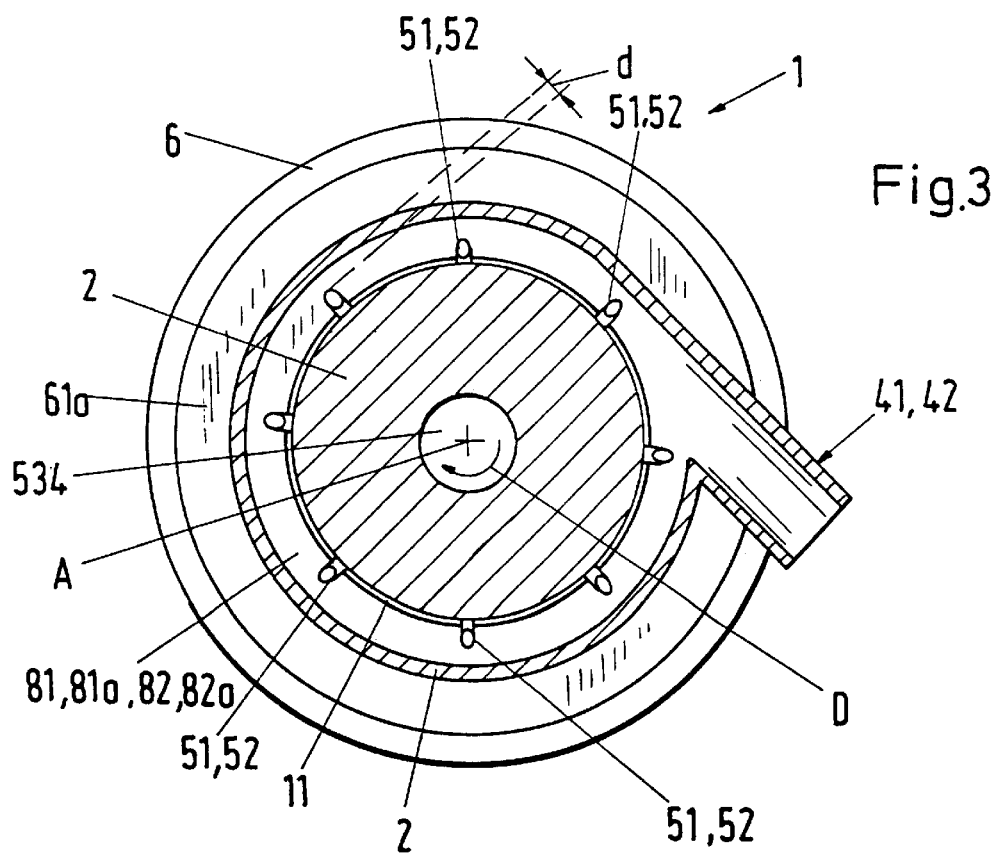
FIG. 3: a cross section through the first embodiment along section lines III—III and IIIa—IIIa in FIG. 1.
Figure 4:
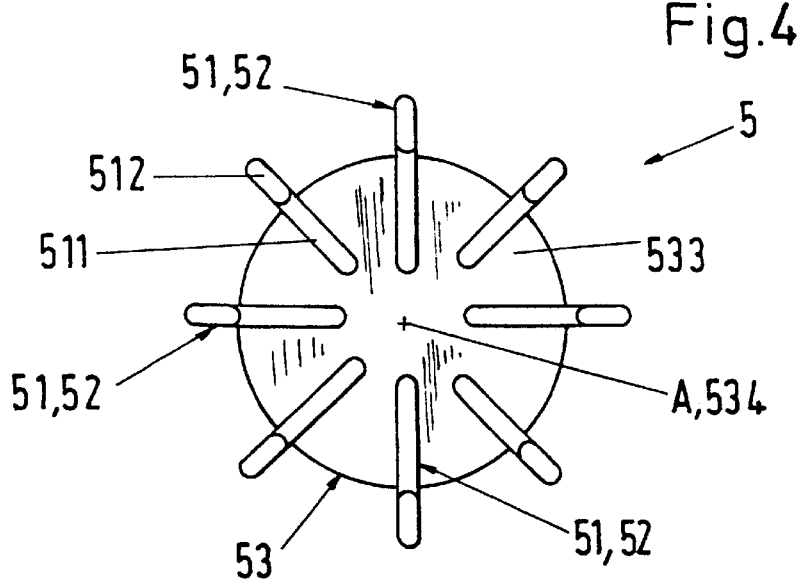
FIG. 4: a top view of the impeller of the first embodiment from the axial direction (cover plate not shown)
Figure 7:
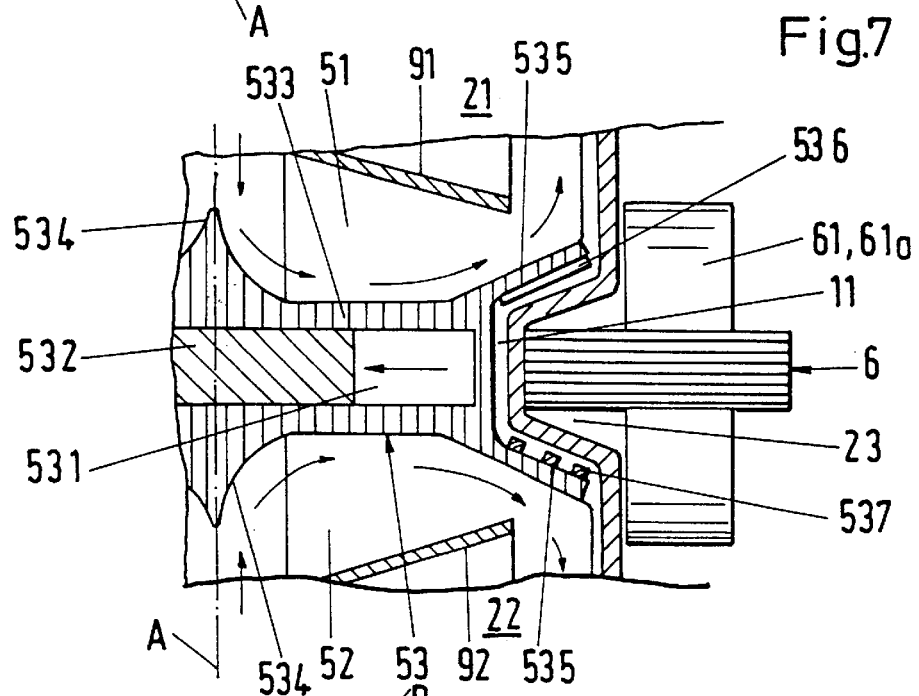
FIG. 7: a detailed view illustrating a further variation in the rotor of the centrifugal pump according to the invention.
Figure 8:
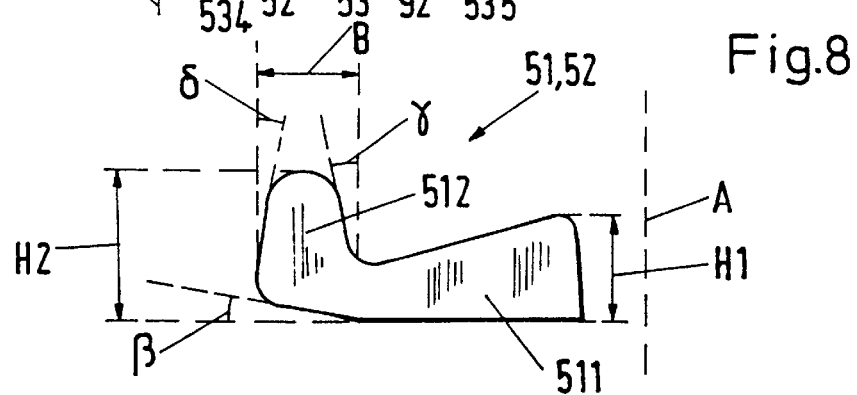
FIG. 8: a side view of a vane of the impeller.

A first embodiment of the centrifugal pump according to the invention, labeled as a whole by reference number 1, is explained in greater detail in FIGS. 1–4 and FIG. 8. FIG. 1 shows the first embodiment in a lengthwise section. For improved understanding, FIGS. 2 and 3 show this embodiment in a cross sectional view as well. In FIG. 2 a cross section is shown which is obtained for both section line II—II and section line IIa—IIa in FIG. 1. The cross section shown in FIG. 3 is obtained for both section line III—III and section line IIIa—IIIa in FIG. 1. FIG. 4 shows a top view of impeller 5 of the first embodiment as viewed in the axial direction. A cover plate 91 or 92, explained in greater detail below (see FIGS. 1, 6, 7) is not shown in FIG. 4. FIG. 8 shows a side view of an impeller 51 or 52.

Pump housing 2 has two inlets 31, 32 arranged as axial inlets, through which the fluid to be delivered enters the pump housing as indicated by arrows E1 and E2. Each of inlets 31 and 32 is connected with a fluid system, not shown. First inlet 31 is connected for example with the pulmonary vein while second inlet 32 is connected with the vena cava in the systemic circulation. The two outlets 41, 42 are designed as tangential outlets through which the fluid leaves pump housing 2 as indicated by arrows 01 and 02. Outlets 41, 42 are also connected with the fluid systems. First outlet 41 is connected with the aorta for example, while the second outlet 42 is connected with the pulmonary artery.

Impeller 5 is located Inside pump housing 2, said impeller comprising rotor 53, in the shape of a disk in this case, as well as two sets of vanes 51 and 52 mounted on the rotor, said vanes preferably being made of plastic. The vanes that belong to the first set have been given reference number 51 and the vanes in the second set have been given reference number 52. For reasons of improved clarity, only two of vanes 51 or 52 are shown for each set in FIG. 1.

Disk-shaped rotor 53 comprises an annular permanent magnet 531 that surrounds rotation axis A, a disk-shaped iron return 532 that fills the hole in annular permanent magnet 531, as well as a jacket 533 preferably made of titanium or plastic. Vanes 51 and 52 are connected nonrotatably with jacket 533. A set of vanes 51 or 52 is provided on each of the axial limiting faces of rotor 53, in other words on its top and bottom sides as shown. According to the drawing in FIG. 1, the first set of impellers 51 is located on the top of rotor 53 and the second set of vanes 52 is on the bottom of rotor 53. The permanent magnet 531 is magnetized diametrically for example, as indicated by the two arrows inside it without reference numbers.

Pump housing 2 is surrounded approximately at its center by bearing and drive stator 6 with electrical windings 61. Electrical windings 61 are shown as end turns 61a. The passive magnetically acting rotor 53 together with stator 6 and the supply and control devices, not shown, forms a bearingless motor, with rotor 53 being actively controllable or drivable relative to rotation around axis A as well as its position in the plane perpendicular to rotation axis A, and is mounted in stator 6 in a magnetically passive fashion by reluctance forces with respect to tilting relative to said plane as well as its axial position.

As is especially clear for FIG. 1, the two outlets according to the invention are arranged offset from one another in the axial direction. Preferably, the first outlet 41, as shown, is located immediately above end turns 61a and the second outlet 42 is shown directly below end turns 61a. In particular, outlets 41 and 42 lie on end turns 61a. This permits an especially compact and space-saving design for centrifugal pump 1. By virtue of the mutual offset of outlets 41 and 42, centrifugal pump 1 according to the invention can assume the function of two pump systems. In the operating state, impeller 5 rotates around rotation axis A. The first set of vanes 51 thus delivers fluid from first inlet 31 to first outlet 41 (first pump system), while second set of vanes 52 delivers fluid from second inlet 32 to second outlet 42 (second pump system).

In the embodiment described here, impeller 5, inside pump housing 2, delimits two essentially separate pump chambers 21, 22, namely top first pump chamber 21 as shown as well as bottom second pump chamber 22 as shown, with each pump chamber 21, 22 being associated with one of inlets 31, 32 and one of outlets 41, 42. An important aspect is that centrifugal pump 1 produces two essentially separate pump systems between which only very slight fluid exchange takes place. This means that fluid coming from first or the second inlet 31 or 32 is delivered primarily, more than 90% for example, to the associated first or second outlet 41 or 42, respectively.

In this way, the centrifugal pump according to the invention can assume the function of the heart, with the first pump system assuming the function of the left ventricle (systemic circulation), for example, and the second pump system assuming the function of the right ventricle (pulmonary circulation). The extremely compact and space-saving design of the centrifugal pump according to the invention is especially advantageous in this respect.

Each of pump chambers 21 and 22 comprises a conducting channel 81 or 82 that is essentially annular and runs in the circumferential direction of the pump housing, said channel connecting inlets 31 or 32 associated with pump chambers 21 and 22 with outlets 41 and 42 associated with the same pump chambers 21 or 22. Thus, each guide channel 81, 82 comprises a partial chamber 81a, 82a that is offset relative to impeller 5 as viewed in the axial direction. In other words, conducting channels 81 and 82 are folded in the axial direction. As shown in the drawing (see FIG. 1) guide channel 81 of first pump chamber 21 is folded upward and guide channel 82 of second pump chamber 22 is folded downward.

Since guide channels 81, 82, by virtue of axially offset partial chambers 81a, 82a, can have sufficient volume for the fluid to be delivered, as an additional advantageous measure, vanes 51, 52 of impeller 5 can be designed so that they extend up to the guide channels 81, 82 associated with them as viewed in the radial direction. This measure results in an increase in the effective vane length so that the performance, especially the delivery capacity, of centrifugal pump 1 can be increased further without the external dimensions of centrifugal pump 1 increasing as well.

Especially preferably, vanes 51, 52 are each made angled (see FIG. 1 and FIG. 8) so that they each have a radial part 511 that extends outward in a straight line or in a curve as well as an adjoining axial part 512, said part 512 extending essentially parallel to rotation axis A of impeller 5 or parallel to the side wall of pump housing 2. Axial part 512 extends up to partial chamber 81a or 82a of guide channel 81 or 82. Vanes 51, 52 therefore are each folded in the axial direction. According to the drawing in FIG. 1, vanes 51 of the first set are folded upward and vanes 52 of the second set are folded downward. By this advantageous measure, the effective vane length is further increased, with the efficiency, especially the delivery capacity, of the centrifugal pump being increased even further without the external dimensions of the centrifugal pump being increased. In particular, thanks to the folded design of vanes 51, 52, the fluid is guided longer by vanes 51, 52, increasing the pressure of the fluid.

It is especially advantageous that there is a plurality of possibilities of adapting both the first pump system (first inlet 31, first set of vanes 51 of first guide channel 81, first outlet 41) as well as the second pump system (second inlet 32, second set of vanes 52, second guide channel 82, second outlet 42) independently hydraulically to the function to be assumed. In the design as a blood pump, especially as an artificial heart, it is necessary for physiological reasons for example for the pump system that replaces the left ventricle (systemic circulation) to deliver a higher pressure than the pump system that replaces the right ventricle (pulmonary circulation). Such hydraulic adaptation is possible in centrifugal pump 1 according to the invention, for example by using different designs for vanes 51 of the first set and vanes 52 of the second set. For this purpose, vanes 51 of one set can have an effective vane length that is different from that of vanes 52 of the other set. For example, vanes 51 of the first set, as viewed in the radial direction, can extend further outward than vanes 52 of the second set or vice versa. It is also possible, as can be seen from FIG. 1, to make axial parts 512 of vanes 51 longer than in vanes 52, in other words, to give them a greater axial height H2 (see FIG. 8) so that they extend further into partial chamber 81a or vice versa. By virtue of this measure as well, different effective vane lengths can be provided for the two sets of vanes 51, 52. According to the drawing in FIG. 1, the first (upper) pump system that has vanes 51 with longer axial parts 512 (greater height H2), with the same throughput and preset rpm of impeller 5, creates a higher pressure at first outlet 41 than the second (lower) pump system does at second outlet 42. When used as an artificial heart, the first (upper) pump system preferably replaces the left ventricle and the second (lower) pump system replaces the right ventricle.

In addition, individual hydraulic adaptation of the two pump systems is also possible by altering the shape, for example axial height Hi (FIG. 8), of radial parts 511 of vanes 51, 52, as well as width B of axial parts 512 in the radial direction, and by the geometric design of pump chambers 21, 22, especially guide channels 81, 82.

In addition, designs of impeller 5 are possible in which the number of vanes 51 in the first set differs from the number of vanes 52 in the second set. It is also possible to design vanes 51 of one set to be angled and vanes 52 of the other set to be non-angled, in other words without an axial part 512 or vice versa.

As is best seen from FIG. 1 and FIG. 3, guide channels 81 and 82 are each designed as an annular chamber, in other words with a cross section that remains essentially constant over its circumference, so that all radially outer ends of vanes 51 or 52 in the normal operating state are located essentially at the same distance d (FIG. 3) from the side wall of pump housing 2.

Alternatively, guide channels 81, 82 can be made as helical chambers extending in the radial direction, so that space d between the radially outer ends of vanes 51, 52 and the side wall of pump housing 2 that delimit guide channels 81, 82 increases as viewed in the rotation direction. The rotation direction is indicated in FIG. 3 by arrow D. Space d is then smallest in the vicinity of the shorter leg of tangential outlet 41 or 42 and increases as viewed in rotation direction D. This design of guide channels 81 and 82 as radial helical chambers takes into account the fact that the volume of the fluid located in each guide channel 81, 82 increases toward outlet 41 or 42 as viewed in rotation direction D.

As viewed in the axial direction, a conical cover plate 91 or 92 (see FIGS. 1, 6, 7) can be located between vanes 51 and 52 of impeller 5 and the inside wall of pump housing 2 facing them, said plate being located for example on vanes 51 or 52 in order to reduce the backflow of the fluid from the respective guide channel 81 or 82 toward the associated inlet 31 or 32. Cover plates 91, 92 extend in the radial direction approximately up to the radial inner limit of the respective guide channel 81 or 82.

For good flow guidance in the two pump systems, rotor 53 preferably has means for guiding the flow of the fluid. These means comprise, for example, (see FIG. 1) two conical elevations 534 in the central area of jacket 533 of rotor 53, with the points of conical elevations 534 each lying approximately on rotation axis A in the operating state. One conical elevation 534 extends upward as shown, in other words toward first inlet 31, while second conical elevation 534 extends downward as shown, i.e. toward second inlet 32.

Pump housing 2 is provided on its exterior, in its area that is central relative to axis A, with a circumferential groove 23 that narrows the internal space of pump housing 2 in the axial direction in which rotor 53 rotates in the operating state. Stator 6 extends into this circumferential groove 23. By this measure, assurance is provided that stator 6 is located as close as possible to rotor 53, which is advantageous as far as drive and magnetic bearing of rotor 53 are concerned, and the constriction of the interior of pump housing 2 also serves to separate the two pump chambers 21 and 22 or the two guide channels 81 and 82. The two guide channels 81 and 82 thus communicate via only a very narrow gap 11 through which only a very small fluid exchange takes place in the operating state, said exchange between the two pump systems of centrifugal pump 1 posing no problems for any application.

In the operating state, impeller 5 rotates around rotation axis A, driven and suspended by the magnetic interaction between rotor 53 and bearing and drive stator 6. As a result, both the first and second pump systems deliver fluid, essentially only from respective inlet 31 or 32 to the associated outlet 41 or 42. It is advantageous in this regard that the impeller is exposed to the fluid on both sides (in the axial direction) and delivers said fluid. This results in at least partial compensation of the axial thrust on impeller 5, so that the axial forces on opposite sides of impeller 5 are eliminated at least partially. Hence, the passive magnetic axial support of impeller 5 is sufficient, especially for high delivery capacities.

Figure 5:
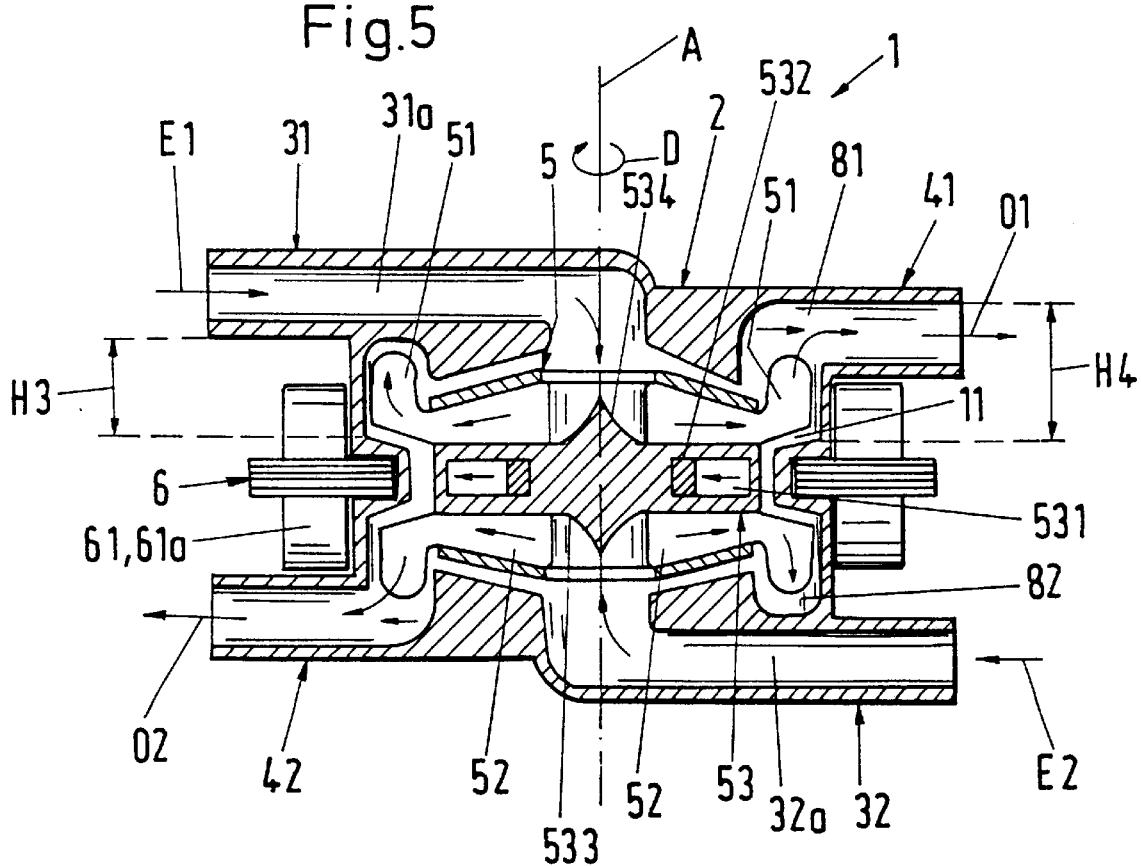
FIG. 5: a lengthwise section through a second embodiment of the centrifugal pump according to the invention.

FIG. 5 shows in a lengthwise section a second embodiment of centrifugal pump 1 according to the invention. In FIG. 5 as well, only two of vanes 51 and 52 are shown for reasons of improved clarity. In the following, only the differences with respect to the first embodiment will be described. Otherwise, the explanations for the first embodiment will apply in logically similar fashion to the second embodiment as well.

In the second embodiment, the axial height H3, H4 of each guide channel 81, 82 increases in the circumferential direction so that each guide channel 81, 82 forms an axial helical chamber. The axial height H3, H4 of guide channel 81 or 82, as viewed in the rotational direction as indicated by arrow D, assumes its minimum value immediately downstream from outlet 41 or 42 and increases continuously in the circumferential direction. At the side opposite outlet 41 or 42, guide channel 81 or 82 has an axial height H3 for example. The axial height then increases further in rotation direction D and reaches its maximum value H4 (H4>H3) at outlet 41 or 42.

The design of guide channels 81, 82 as axial helical chambers is especially advantageous from the flow engineering aspect, especially in combination with angled vanes 51 and 52.

Of course, designs are also possible in which guide channels 81, 82 are designed as radial as well as axial helical chambers, in other words, as viewed in the circumferential direction, they expand radially and at the same time have an increasing axial height.

It is also possible to make the two guide channels 81 and 82 different.

Another difference in the second embodiment consists in the design of inlets 31, 32. Each inlet 31, 32 comprises an angled inlet channel 31A or 32A that extends initially essentially radially with respect to rotation axis A and then curves toward rotation axis A, so that the fluid in each case can travel from the axial direction to impeller 5 as indicated by arrows E1 and E2 in FIG. 5. As FIG. 5 shows, the radially extending part of inlet channel 31a or 32a is guided to rotation axis A from a side that is different from the side toward which associated outlet 41 or 42 extends. This measure, especially in combination with the design of guide channel 81 or 82 as an axial helical chamber, permits an especially compact design of centrifugal pump 1. Since guide channel 81 or 82 has a smaller axial height H3 on the side opposite corresponding outlet 41 or 42 than on the side where corresponding outlet 41 or 42 is located (axial height H4), the radially extending part of corresponding inlet channel 31a or 32a can be located closer to impeller 5 relative to the axial direction, especially in such fashion that the radially extending part of inlet channel 31a or 32a and the associated outlet 41 or 42 overlap at least partially in terms of their axial positions, with inlet channels 31a and 32a preferably being integrated into pump housing 2. By this measure, centrifugal pump 1, because of the optimized utilization of the available space, has an extent in the axial direction that is as small as possible, making it very compact and thus permitting high delivery capacity.

In addition, in the second embodiment, the two outlets 41 and 42 are offset relative to the circumferential direction of pump housing 2, by about 180° as shown. This is especially advantageous for blood pumps in that the two pump systems of centrifugal pump 1, when installed in the body, can be better connected with the respective blood vessels, namely the vena cava and the pulmonary artery and the pulmonary vein and the aorta, respectively. The mutual offset of outlets 41 and 42 and inlets 31 and 32 by 180° is of course to be understood as merely an example. Other angles are quite possible. In particular the position of inlets and outlets 31, 32, 41, and 42 can be adapted to the physiological conditions or individually to the patient.

In the second embodiment, the iron return 532 in the rotor is not designed as a disk but as a ring that is located concentrically and radially inside permanent magnet 531.

In the following, several advantageous design variations will be described that can be used in both embodiments.

Figure 6:
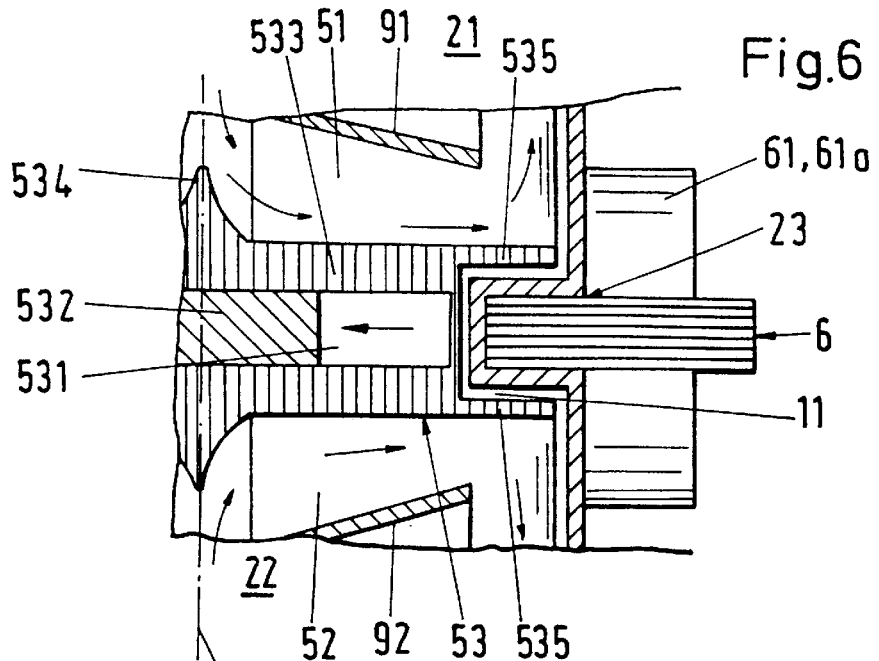
FIG. 6: a detailed view to illustrate a variation on the rotor of the centrifugal pump according to the invention.

The detailed view in FIG. 6 illustrates one variation of the design of rotor 53. Here, jacket 533 of rotor 53 has two projections on its radially outer end, said projections extending as shown above and below circumferential groove 23. By this measure, gap 11 that connects the two pump chambers 21 and 22 is extended and a labyrinth seal effect can be achieved. This results in an improved sealing of the two pump chambers 21 and 22 off from one another, with the fluid exchange between the two pump systems being further reduced.

In the version shown in FIG. 7, projections 535 of jacket 533 extend diagonally relative to the radial direction in other words at an oblique angle relative to rotation axis A. Upper projection 535 runs diagonally upward as shown in the drawing, and lower projection 535 runs diagonally downward as shown in the drawing. Preferably, circumferential groove 23 is designed so that it follows the bevel of projection 535. The beveling of projections 535 is another means of improving flow guidance.

It can also be advantageous to provide additional vanes 536 and/or helical elevations or depressions 537 on the sides of projections 535 facing gap 11. These serve as means of avoiding fluid stagnation. By means of additional vanes 536 or helical elevations or depressions 537, a situation can be created such that the fluid located in gap 11 is delivered as well. In the specific case of blood pumps, this avoids the risk of formation of thrombi. The means for avoiding fluid stagnation 536, 537 can be provided either on both projections 535 or on only one of projections 535.

FIG. 8 shows a variation on vanes 51, 52 in a detailed view. In this design, the radially outer ends of vanes 51, 52, on their sides facing corresponding inlets 31 or 32 (in FIG. 8, these are the undersides of vanes 51, 52) are beveled at an angle $\beta$ relative to the rotation plane that extends perpendicularly to rotation axis A. As a result, a situation is avoided in which vanes 51, 52 strike pump housing 2 following a slight tilting of impeller 5. Preferably, axial parts 512 of vanes 51, 52 are also beveled at their radially inner and/or radially outer limits at an angle of $\gamma$ or $\delta$ relative to the direction of rotation axis A in order to prevent vanes 51, 52 from striking during slight tilting relative to the rotation plane. For practical reasons, angles $\beta$, $\gamma$, and $\delta$ of the bevels are preferably each smaller than 10° and especially smaller than 5°. In particular, designs are preferred in which all three angles $\beta$, $\gamma$, and $\delta$ have the same value.

Figure 9:
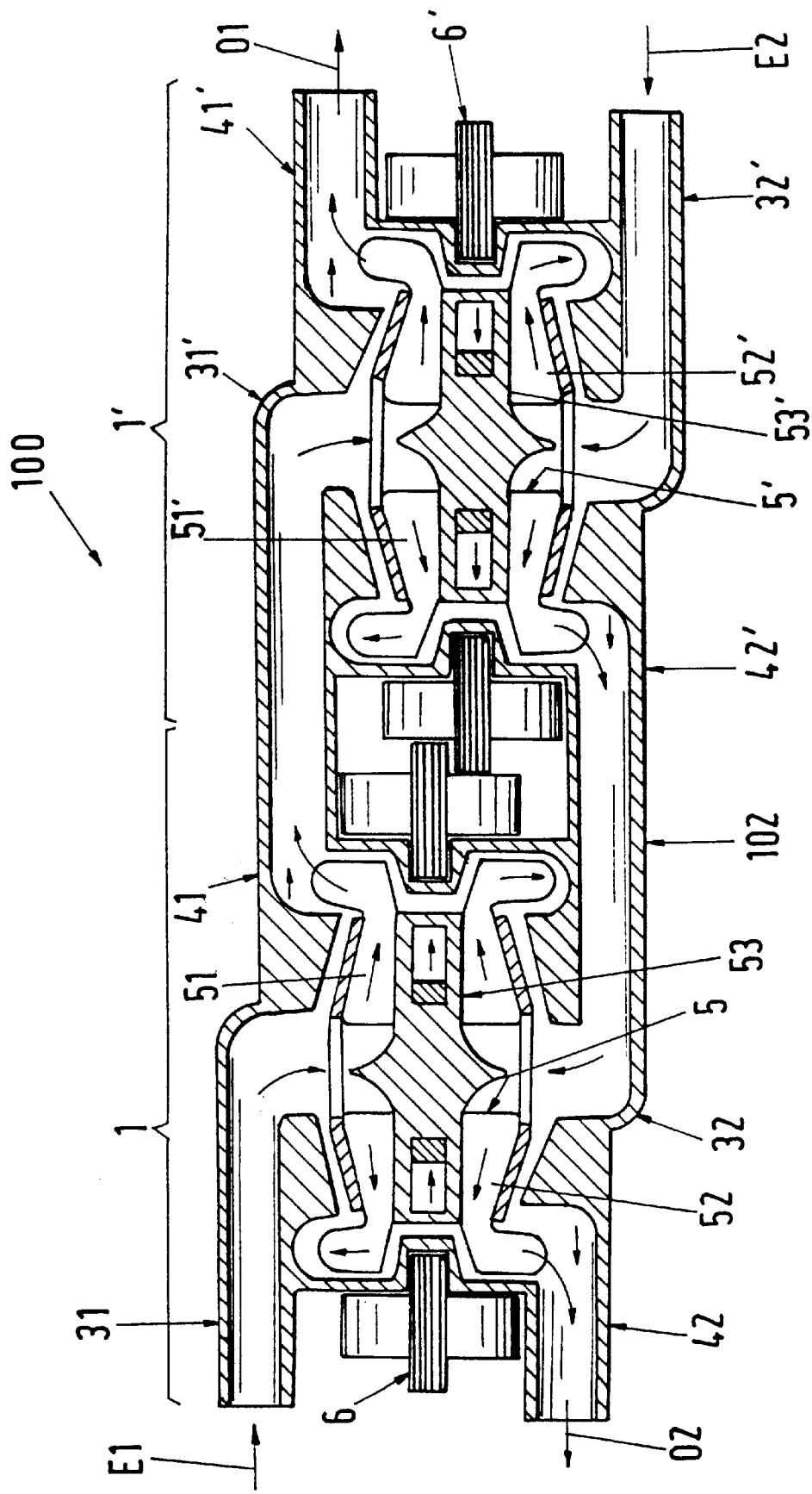
FIG. 9: a lengthwise section through a first embodiment of the centrifugal pump system according to the invention.

FIG. 9 shows a lengthwise section through a first embodiment of the centrifugal pump system according to the invention, labeled as a whole by reference number 100. Centrifugal pump system 100 comprises at least two centrifugal pumps 1 and 1'. The reference numbers have the same meanings as explained above in conjunction with centrifugal pump 1. To distinguish between the two centrifugal pumps 1 and 1', the reference numbers that relate to centrifugal pump 1' have each been given a prime but those that have the same element as the corresponding reference number have no prime. Centrifugal pump system 100 (FIG. 9) comprises the two centrifugal pumps 1 and 1' which are each designed according to the second embodiment (FIG. 5). The inlets of system 100 are first inlet 31 of first centrifugal pump 1 and second inlet 32' of second centrifugal pump 1'. The outlets of system 100 are first outlet 41' of second centrifugal pump 1' and second outlet 42 of first centrifugal pump 1. First outlet 41 of first centrifugal pump 1 is connected with first inlet 31' of second centrifugal pump 1' and second outlet 42' of second centrifugal pump 1' is connected with second inlet 32 of first centrifugal pump 1. In this fashion, centrifugal pumps 1, 1' are connected together to form a hydraulic series circuit.

It is possible to locate the two centrifugal pumps 1, 1' in a common pump housing 102.

Such an arrangement 100 is especially advantageous for those applications in which maximum operating reliability is required. In particular, such a system is also suitable as a blood pump, especially an artificial heart. If one of the two centrifugal pumps 1, 1' fails, the other will take over proper operation of the system, since each of centrifugal pumps 1 and 1' alone is able, because of its delivery capacity and because of the feature according to the invention of providing two pump systems, to take over the function of the heart. The redundancy provided by the series connection thus means a considerable increase in operational reliability. In addition, the extremely compact design of centrifugal pumps 1, 1' according to the invention also permits a very compact design of system 100,. The entire system 100 for example, can be so designed that its axial height is about 45 mm and its extent in the radial direction does not exceed 120 mm by 60 mm. Despite this extremely compact design, each of centrifugal pumps 1, 1' provides a maximum delivery capacity greater than that of the human heart.

Figure 10:
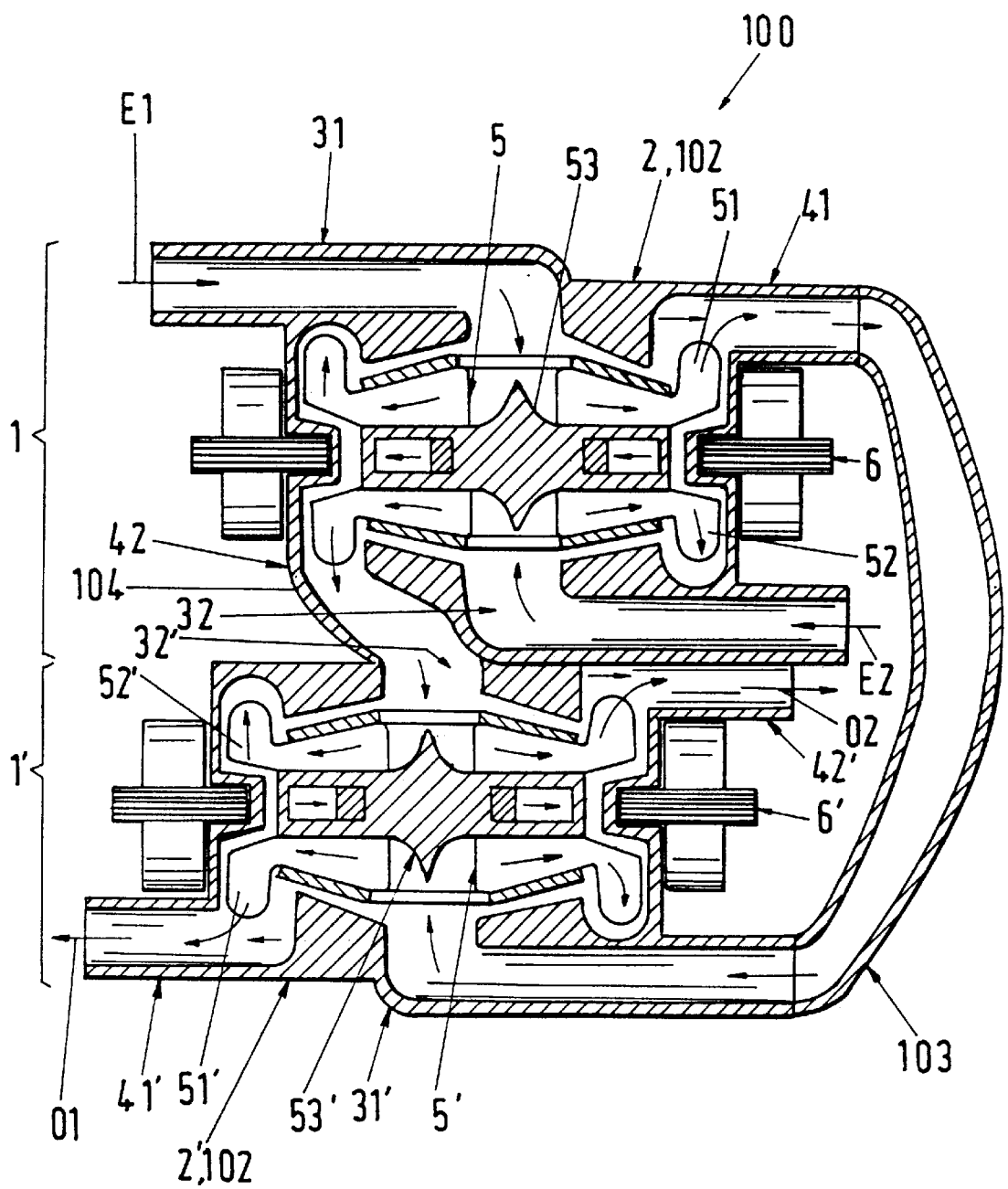
FIG. 10: a lengthwise section through a second embodiment of the centrifugal pump system according to the invention.

FIG. 10 shows a lengthwise section through a second embodiment of centrifugal pump system 100 according to the invention. Here again, two centrifugal pumps 1 and 1' are provided, connected hydraulically in series. In the diagram in FIG. 10, the second (lower) centrifugal pump 1' is inverted (relative to the view in FIG. 5), in other words, in this figure, first inlet 31' and first outlet 41' are shown at the bottom in the drawing. The two inlets 31 and 32 of first centrifugal pump 1 are used as inlets for system 100. The two outlets 41' and 42' of second centrifugal pump 1' are used as outlets of system 100. First outlet 41 of first centrifugal pump 1 is connected with first inlet 31' of second centrifugal pump 1' as indicated symbolically by hose 103. Second outlet 42 of first centrifugal pump 1 is connected with second inlet 37' of second centrifugal pump 1', as indicated symbolically by connection 104.

In a design of centrifugal pump system 100 (FIG. 9, FIG. 10) as a blood pump for example, the first inlet of system 100 (first inlet 31 of first centrifugal pump 1) is connected with the vena cava while the second inlet of system 100 (second inlet 32' of second centrifugal pump 1' or second inlet 32 of first centrifugal pump 1) is connected with the pulmonary vein, and the first outlet of system 100 (first outlet 41' of second centrifugal pump 1') is connected with the aorta and the second outlet of system 100 (second outlet 42 of first centrifugal pump 1 and second outlet 42' of second centrifugal pump 1') is connected with the pulmonary artery.

Of course, centrifugal pump systems are also possible in which the centrifugal pumps are connected hydraulically in parallel. In theory, the achievement of redundancy by connecting two pumps together is not limited to the pumps described here.

The centrifugal pump according to the invention is especially characterized by the fact that it provides two pump systems that are essentially separate in a single pump which is extremely compact and space-saving in design and also permits a high delivery capacity whose maximum values are above the delivery capacity of the human heart. The centrifugal pump according to the invention is therefore suitable as a blood pump, especially as an artificial heart for applications inside and outside the body. By virtue of the centrifugal pump system according to the invention, a very reliable system is provided that can also assume the function of the heart inside or outside the body.

What is claimed is:

1. A centrifugal pump for delivering a fluid, with a pump housing that has a first and a second inlet as well as a first and second outlet for the fluid, with a magnetically mounted impeller located inside pump housing, said impeller being rotatable around a rotation axis and comprising a magnetically effective rotor in the shape of a disk or ring, as well as two sets of vanes, with a set of vanes being provided on each of the two axial boundary surfaces of rotor, wherein the two outlets are offset with respect to one another in the axial direction.

2. A centrifugal pump according to claim 1, in which impeller delimits two essentially separate pump chambers in the interior of pump housing, and each pump chamber is associated with one of inlets and one of outlets.

3. A centrifugal pump according to claim 2, with each pump chamber comprising a guide channel that is essentially annular and runs in the circumferential direction of the pump housing, said channel connecting inlets associated with pump chambers with outlets associated with the same pump chambers, with each guide channel comprising a partial chamber which is offset relative to impeller as viewed in the axial direction.

4. A centrifugal pump according to claim 1, with a stator surrounding pump housing, said stator having electrical windings, with stator further being designed as a bearing and drive stator, so that impeller is drivable in the operating state by the magnetic interaction between stator and rotor and can also be mounted with zero contact in pump housing.

5. A centrifugal pump according to claim 4 with rotor being actively controllable or drivable in the operating state by means of electrical windings of stator with respect to three degrees of freedom and being mounted magnetically passively with respect to three additional degrees of freedom by reluctance forces in stator.

6. A centrifugal pump according to claim 1 with vanes each being angled, so that they each have a radial part that extends outward in the radial direction in a straight line or in a curve, as well as an adjoining axial part that extends essentially parallel to rotation axis of impeller.

7. A centrifugal pump according to claim 1 with vanes of one set having a different effective vane length than vanes of the other set.

8. A centrifugal pump according to claim 1 with the two outlets being offset in the circumferential direction of pump housing.

9. A centrifugal pump according to claim 1 with axial height of each guide channel increasing in the circumferential direction.

10. A centrifugal pump according to claim 1 with each inlet comprising an angled inlet channel which initially extends radially with respect to rotation axis and then curves toward rotation axis so that fluid can move from the axial direction to impeller.

11. A centrifugal pump according to claim 1 with rotor having means for guiding the flow of the fluid.

12. A centrifugal pump according to claim 1 with means being provided to avoid fluid stagnation.

13. A blood pump with a centrifugal pump, the centrifugal pump comprising:

a pump housing that has a first and a second inlet as well as a first and a second outlet for the fluid, with a magnetically mounted impeller located inside pump housing, said impeller being rotatable around a rotation axis and comprising a magnetically effective rotor in the shape of a disk or ring, as well as two sets of vanes, with a set of vanes being provided on each of the two axial boundary surfaces of rotor, wherein the two outlets are offset with respect to one another in the axial direction.

14. A blood pump in accordance with claim 13 wherein the blood pump is an artificial heart.

15. A blood pump comprising a centrifugal pump system, the centrifugal pump system comprising two centrifugal pumps, wherein each centrifugal pump comprises:

a pump housing that has a first and a second inlet as well as a first and a second outlet for the fluid, with a magnetically mounted impeller located inside pump housing, said impeller being rotatable around a rotation axis and comprising a magnetically effective rotor in the shape of a disk or ring, as well as two sets of vanes with a set of vanes being provided on each of the two axial boundary surfaces of rotor, wherein the two outlets are offset with respect to one another in the axial direction.

16. A centrifugal pump system comprising at least two centrifugal pumps, wherein each centrifugal pump comprises:

a pump housing that has a first and a second inlet as well as a first and a second outlet for the fluid, with a magnetically mounted impeller located inside pump housing, said impeller being rotatable around a rotation axis and comprising a magnetically effective rotor in the shape of a disk or ring, as well as two sets of vanes with a set of vanes being provided on each of the two axial boundary surfaces of rotor, wherein the two outlets are offset with respect to one another in the axial direction.

17. A centrifugal pump system according to claim 16 wherein the centrifugal pumps are connected with one another in such fashion to form a hydraulic series circuit.

* * * * *